United States Patent
Xie et al.

(10) Patent No.: US 9,445,624 B2
(45) Date of Patent: Sep. 20, 2016

(54) ANTI-FATIGUE COMPOSITION OF PLANT MATERIAL AND PREPARATION METHOD, USE AND PRODUCTS THEREOF

(76) Inventors: Chen Xie, Beijing (CN); Zhong Zhong, Beijing (CN)

(*) Notice: Subject to any disclaimer, the term of this patent is extended or adjusted under 35 U.S.C. 154(b) by 324 days.

(21) Appl. No.: 13/814,129

(22) PCT Filed: Aug. 5, 2010

(86) PCT No.: PCT/CN2010/075741
§ 371 (c)(1),
(2), (4) Date: Aug. 12, 2013

(87) PCT Pub. No.: WO2012/016384
PCT Pub. Date: Feb. 9, 2012

(65) Prior Publication Data
US 2014/0057002 A1    Feb. 27, 2014

(51) Int. Cl.
| | |
|---|---|
| *A61K 36/185* | (2006.01) |
| *A61K 36/41* | (2006.01) |
| *A61K 36/42* | (2006.01) |
| *A61K 36/81* | (2006.01) |
| *A23L 2/52* | (2006.01) |
| *A23L 1/30* | (2006.01) |
| *A61K 36/424* | (2006.01) |
| *A61K 36/815* | (2006.01) |

(52) U.S. Cl.
CPC ............... *A23L 2/52* (2013.01); *A23L 1/3002* (2013.01); *A61K 36/41* (2013.01); *A61K 36/424* (2013.01); *A61K 36/815* (2013.01)

(58) Field of Classification Search
None
See application file for complete search history.

(56) References Cited

U.S. PATENT DOCUMENTS 7,923,044 B2 *  4/2011  Bias ............................. 424/725
2008/0124416 A1 *  5/2008  Moffett ........................ 424/777

FOREIGN PATENT DOCUMENTS

| CN | 1376427 A | * | 10/2002 |
| CN | 101595988 A |   | 12/2009 |
| CN | 101804123 A |   | 8/2010 |
| KR | 2009066682 A | * | 6/2009 |

OTHER PUBLICATIONS

English abstract for CN-101804123.
English abstract for CN-101595988.

* cited by examiner

*Primary Examiner* — Chris R Tate
*Assistant Examiner* — Randall Winston
(74) *Attorney, Agent, or Firm* — Fishman Stewart PLLC

(57) ABSTRACT

The present invention provides a composition of a plant material with anti-fatigue activity, its preparation method, usage and related products. The said composition is manufactured from the following plant materials: 20-80% from the genus *Rhodiola*; 10-60% *Gynostemma*; 10-60% *Lycium*. The said composition can be used to manufacture health product, food or anti-fatigue medicine which is able to significantly reduce the fatigue symptoms of those people suffering from fatigue, improve sleeping quality with no impact on normal body physiology. It is shown that the medicine derived from the present is invention exerts its anti-fatigue effect through improving the functions of erythrocytes and thrombocytes to enhance the body's ability of supplying oxygen. The medicinal composition of the present invention is characterized by the small effective dose and good water solubility and thus suitable to be made into a variety of dosage forms for use.

9 Claims, 2 Drawing Sheets

ANTI-FATIGUE COMPOSITION OF PLANT MATERIAL AND PREPARATION METHOD, USE AND PRODUCTS THEREOF

TECHNICAL FIELD

The present invention relates to a medicinal composition of pure botanical origin in the field of application of modern botanical medicine.

BACKGROUND

Fatigue is sometimes defined as "the awareness of a decreased capacity for physical and mental activity due to imbalance in the availability, utilization, and restoration of resources needed to perform activity". It is a complex and subjective phenomenon often assessed through self-statement. The main symptoms of fatigue include one or more of the following: lack of energy, tiredness and sleepy, headache, dizziness, muscle weakness, slow response, poor judgment, depression, loss of appetite, decreased immunity and memory ability, trouble concentrating, compromised desire to initiate activities, etc. Fatigue occurs commonly in people of all walks of life while patients suffering from acute or chronic diseases often feel fatigue of various degrees. At the same time, healthy people could have symptoms of fatigue due to all kinds of causes, including 1. Deprived Sleep Generally an adult requires 8 hours sleep everyday but many people cannot meet the requirement resulting in tiredness. This type of sleep deficiency usually happens under the following two circumstances: a) various practical reasons related to work, family and society. Too fast a pace of lifestyle of many people forced them to sleep less and less, failing to meet one's physiological requirement. In addition, people during some specific time could feel tiredness. For example, People looking after new-born babies or patients at night often do not have sound sleep; b) a more common cause of sleep deficiency mainly related to ageing. From quinquagenarian to elderly, people's body function undergo gradual degeneration which includes the slow change of the biological clock responsible for sleep. Around dusk, a drowsy feeling often crept over many elderly people, who also wake up before dawn, with increasing number of waking-ups during sleep, longer period of time required to fall asleep again and the duration of deep sleep, an important indicator for sleep quality, getting shorter and shorter. According to a research report by Harvard Medical School (Harvard Medical School Special Health Report <<Boosting Your Energy>>, Harvard Health Publications), the deep sleep time every night of 30 year old people is about 50% of that of 20 year old while that of 65 year old less than 20% with only 5% of deep sleep of whole sleep time. Lowered sleep quality resulted in insufficient energy and becoming more likely to feel fatigue.

2. Too Little Exercise

Lacking of regular exercise for a long time or sitting every day for too long without much activity makes people easily feel tired soon after they start some physical activity.

3. Imbalanced Diet

Some people are very susceptible to feeling of fatigue due to insufficient energy or malnutrition which may be a result of having only low sugar, low calorie food or overly picking on what to eat for such reasons as slimming, etc. Others have a habit of having high calorie food such as chocolate to supplement energy. This may produce a short burst of energy supply but the effect is likely to diminish very quickly resulting in increased feeling of fatigue.

4. Bad Habit Such as Alcoholism

Alcohol inhibits nerve system making prolonged reaction time and also disturbs sleeping mode. Smoking or drinking caffeine containing drinks will have stimulating effect on nerve system causing insomnia leading to feeling of fatigue. Although many people keep those habits for temporal refreshing, the final result is to make them feel more of fatigue.

5. Psychological Pressure

Abnormal mental state is one of the important causes of fatigue. It is now very common for people feel psychological pressure or stressed for work or family related reasons such as heavy work load, big change in job responsibility, bad working environment, no job security, illness, family misfortune, etc.

6. Bad Working Environment

Bad working environment will increase the feeling of fatigue, such as mining area, plateau oxygen-deficient environment, work place too cold or too hot, too noisy or too quiet, no one to talk to, irregular shift, focusing doing the same thing repeatedly. etc. Fatigue could greatly disturb people's normal life and have massive negative impact on quality of life. Long-term fatigue could become a potential "killer" of health or even life. The main impacts of fatigue upon human physiology can be summarized as follows:

(1) Inhibition on CNS Functions

Under the state of fatigue, the human CNS is likely to be underperforming due to the inhibited secretion of such neurotransmitters as serotonin, dopamine and acetylcholine, which will lead to slow response, poor judgment, muscle weakness and becoming distractive. If this happened to a driver at the wheel, the consequence could be very serious.

(2) Compromised Immune System Functions

Immune system plays a defending role in our body. Under normal situation, it effectively protects us from the bad impact of harmful factors such as bacteria, virus or hazardous chemicals. However, if the immune function was compromised due to fatigue, the body's resistance to various hazardous factors will be weakened. A typical example is that people in fatigue become prone to upper respiratory tract infection. On the other hand, normal people will have their immunity decreased and some cell factors increased after acute virus or bacterial infection, causing increased feeling of fatigue. It can be seen that inhibited immune system could be either the cause or the consequence of fatigue. There for, an essential approach to combat fatigue is to regulate the immune is system and strengthen immunity.

(3) Impact on Oxygen Supply by Blood System and Reducing Body Energy Supply

The decomposition of blood glucose in vivo will release energy. With sufficient oxygen it will decompose into $CO_2$ and water, at the same time release large amount of energy. By contrast, insufficient supply of oxygen will lead to less energy released and a lot of toxic waste produced through the decomposition of glucose. Researches showed that in the state of fatigue, the amount of oxygen supplied to muscles was greatly reduced and the muscle was in effect in a state of oxygen deprivation. If the oxygen deprivation happened to heart muscle for a long time the consequence could be devastating. Furthermore, because other body activities also require oxygen it is essential to have a continuous supply of oxygen to all the tissues in order to maintain the normal vitality of all the systems of the body. Therefor increasing oxygen supply to tissues will help the energy supply to the body, which in turn will assist the recovery from fatigue and reduce the risk of becoming ill.

In terms of combating fatigue there exist a number of approaches, including taking a holiday, finding an satisfactory job, regular exercise, changing to a better diet and sufficient sleep. However, because of certain objective reasons, the measures taken to combat fatigue had not brought about the expected effect for many people. Firstly, it's not easy for people to change their lifestyle or social role. How a person is to live his/her life has already been defined by the related realities such as duty at work, family responsibility, social interaction, financial situation, etc. Secondly, people with long term fatigue may have undergone certain physiological changes including disorder of nerves system and endocrine system, weakened immunity, abnormal blood system, digestion disorder, etc. When these happened, it would be difficult to rely solely on the self-repair function of the body to get things right. And at this stage, a very essential and significant intervention to be considered is the use of some effective, safe and natural health products to help individual system recover to normal.

"Adaptogen" medicine is now widely accepted in the western medical world as a type of products having anti-fatigue effect. The concept of "adaptogen" was first introduced in 1947 by a Russia scientist, Nikolai Lazarev. It referred to a group of natural botanical products which was believed to be able to help human body return to normal through assisting its non-specific defense function against pressure and stimulation. They were considered safe and non-toxic within normal dose range and could systematically adjust and regulate human body. The most striking difference between "adaptogen" medicine and other drugs lies in that the former is able to effectively balance the secretion of hormones and immune system through antagonizing the hyper-function and strengthening the hypo-function leading to enhanced immunity and reduced feeling of fatigue. Consequently, we can consider the use of adaptogen type of botanical products to improve the vitality and sleep quality of middle-aged and elderly people through adjusting, balancing and optimizing the hormone levels and immune system.

Foreign researchers speculated that adaptogen type of drugs worked in a similar way to the "qi tonifying" herbs in traditional Chinese medicine (TCM). According to the theory of TCM, the feeling of fatigue, especially long term fatigue, is caused by "deficiency", mostly "qi deficiency" or both "qi and yin deficiency". "Qi deficiency" can lead to the accumulation of water, dampness and phlegm, blood stagnation, which will further result in the consumption of qi and yin, and causing insomnia at night and lack of energy on the day. In addition, with ageing both qi and blood system are getting weak, people are more likely to experience the symptoms of qi and yin deficiency, mainly manifested as insomnia and fatigue. TCM practitioners commonly treat those people with qi and yin tonifying herbs such as *Lycium* fruit together with other herbs of relevant property or function to adjust body system in order to improve sleep and reduce fatigue.

*Rhodiola, Gynostemma* and *Lycium* plants are commonly regarded as "adaptogen" herbs, which are also classified as having qi-tonifying property in Chinese *Materia Medica*. Individual herb extracts of the three are now marketed, respectively, as anti-fatigue products but with different "adaptogen" actions due to the different chemical constituents that each herb contains. For example, *Rhodiola* has renowned function of rectification for many body systems. *Gynostemma* showed significant sedative, hypnotic and analgesic actions and could effectively improve sleep while *Lycium* is a traditional anti-ageing tonic used to enhance physique and delay ageing. When combined, the 3 herbs will act with different mechanisms of action to achieve better anti-fatigue result and at the same time to reduce the amount of individual herbs required. This will also improve the safety profile of the finished product allowing for longer term use than those single herb products.

Most of the marketed single herb products mentioned above do not have safety and/or efficacy evaluation, or explicit quality standards to ensure the consistency of the products. By contrast, the inventors of the present invention carried out strict toxicological and clinical studies, which comprehensively demonstrated the clinical safety and efficacy of the product of the present invention. Furthermore, the inventors of the present invention established, through experimental studies, specific quality standards and manufacturing process to guarantee the stability and batch-to-batch consistency of the product. The pharmaceutical and clinical studies carried out also resulted in the determination of the safe and effective dose range of the product for human use in the field of anti-fatigue.

SCOPE OF THE INVENTION

The first aspect of the present invention is to provide a composition of plant materials with anti-fatigue effect. It improves people's sleep, provide energy and significantly reduce the feeling of fatigue.

The second aspect of the present invention is to provide a safe and small dose anti-fatigue product, which can be taken for a long period of time without toxic or side effect.

The third aspect of the present invention is to provide the usages of above said composition in manufacturing relevant food, medicine and health products.

In another aspect, the afore said composition made from botanical materials and having anti-fatigue effect is manufactured using the botanical materials from the plants of genera *Rhodiola, Gynostemma* and *Lycium*.

In another aspect, in order to achieve better anti-fatigue effect, the said composition comprises 20-80% plant material from the genus *Rhodiola;* 10-60% *Gynostemma;* 10-60% *Lycium*, calculated on the basis of the dry weight of the raw materials and preferably, 30-50% from the genus *Rhodiola;* 20-40% *Gynostemma;* 20-40% *Lycium*.

In another aspect, the said *Rhodiola* plants can be one or more of the following species: *Rhodiola sachalinensis* A. Bor., *R. rosea* L., *R. crenulata* (Hook. f. et Thoms.) H. Ohba, *R. kiriloii* (Regel) Maxim, with *R. sachalinensis* being the preferred species.

In another aspect, the said *Gynostemma* plants can be one or more of the following species: *Gynostemma pentaphyllum* (Thunb.) Makino, *G. laxum* (Wall) Cogn., *G. pubescens* (Gagnep) C. Y. Wu, *G. gunagxiense* X. X. Chen et D. H. Qin, *G. compressum* X. X. Chen et D. R. Lians, with *G. pentaphyllum* being the preferred species.

In another aspect, the said *Lycium* plants can be one or more of the following species: *Lycium barbarum* L., *L. chinense* Mill. and *L. dasystemum* Pojark with *L. barbarum* being the preferred species.

In another aspect, any parts of the above said plant species can be used to obtain the botanical composition of the present invention. In order to obtain the best quality extracts, the preferred parts from each plant are:

Root and/or rhizome of *Rhodiola*
Rhizome and/or whole herb of *Gynostemma*
Dried ripe fruit of *Lycium*

In another aspect, the essential constituents of the said botanical composition comprise the total extracts of each said plant raw material or the mixtures thereof. For example, *Rhodiola* extract can be obtained by extracting the mixed raw materials of two or more *Rhodiola* species or, mixing the extracts of individual *Rodiola* plants. This also applies to the *Gynostemma* and *Lycium* extract.

In another aspect, because a variety of extraction methods can be employed to obtain the said composition with the use of the above said ratio of each herb material, the active constituents of the composition may vary. In addition, different species from the same genus or the same species from different production sides may also contain more or less of the active constituents to be extracted. However, these variations in the content of the active constituents won't have great impact on the realization of the aims of the present invention. Based on the above said ratio of each plant material and using routine methods for extraction, the resulted in extracts will contain certain amount of the active constituents to fulfill the requirements to a degree of the present invention.

In another aspect, in order to improve and control the quality of the extracts, reduce the impact of the above mentioned variation due to source material, the inventors of the present invention have defined the quantities of the relevant active/marker chemicals/constituents as follows:

The said *Rhodiola* extract contains 0.5-3.0%, preferably 0.8-2.0% salidroside; the said *Gynostemma* extract contains 20-80%, preferably 20-40% gypenosides; and the said *Lycium* extract contains 20-60%, preferably 30-40% *lycium* polysaccharides.

In another aspect, to obtain the above said botanical composition, one could use any currently available methods but the preferred methods include pulverization, extraction, condensation, drying and mixing.

In another aspect, the preferred extraction solvents include water and/or low molecular alcohol or the mixture of the two and ethanol of pharmaceutical or food grade is the preferred low molecular alcohol. In another aspect, the yields of the extract, expressed as the weight of the raw plant material:the weight of the extract, should be 20:1 to 2:1 and preferably 10:1 to 3:1.

In another aspect, the preferred method for extraction is reflexing and the quantity of the extraction solvent is 5-18 folds, preferably 7-12 folds, of the weight of the raw plant material with a reflexing time of 1-3 hours, preferably 1-2 hours, for 1-5 times, preferably 2-3 times.

In another aspect, excipients can be added to the said botanical composition of the present invention for the manufacturing of health products, food or anti-fatigue medicine and any excipients appropriate to health product, food or anti-fatigue medicine, respectively, may be chosen by people in the art without any creativity but still within the scope of the present invention.

In another aspect, when the said composition is to be made into health products or anti-fatigue medicines, the recommended daily dose is 100-800 mg, preferably 150-600 mg.

In another aspect, the present invention also provides 3 types of products which contain the said composition and excipients.

One of the said products is health product, which contains, in addition to the said composition, relevant excipients of pharmaceutical grade with preferred dosage form of tablets, capsules, oral liquids or soft drinks. When the said product is food, preferably in a form of soft drinks, the excipients to be added to the composition are food additives.

When the said product is anti-fatigue medicine, pharmaceutical grade excipients should be used with preferred dosage forms of tablets, capsules or oral liquids.

In another aspect, the present invention also provides the usages of anti-fatigue medicine and health products which contain the said composition.

DETAILED DESCRIPTION OF THE PRESENT INVENTION

In one embodiment, the composition of the current invention comprises plants from the genera of *Rodiola, Gynostemma* and *Lycium*.

*Rhodiola* plants are now commonly recognized as adaptogen medicinal herb, which is capable of effectively adjusting body function and strengthening its defense ability against harmful factors. Animal experiments demonstrated that under the influence of *Rhodiola* the abnormal CNS transmitter content could be corrected or back to normal. It was capable of improving cardiac function and to certain extent correcting the disorder of hemodynamics cause by blood and oxygen deficiency, resulting in enhanced endurance against oxygen deficiency. Through adjusting the immune system it improved people's ability to adapt different environmental conditions. In 1976, Russia approved the clinical use of *R. sachalinensis* for the treatment of severe fatigue, senile heart failure, different types of psychoneurosis, symptoms caused by autonomic nerve system disorder and the side effects of psycho-drugs. In general, *Rhodiola* possesses some special property in correcting the functions of many body systems. Modern researches discovered that the main active chemical of *Rhodiola* is salidroside with the following structure.

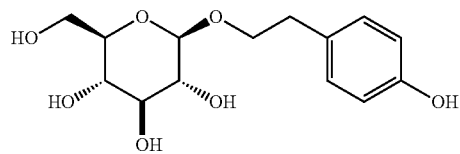 [SMILES: OC[C@H]1O[C@@H](OCCc2ccc(O)cc2)[C@H](O)[C@@H](O)[C@@H]1O]

Although *Gynostemma* is also commonly recognized as another adaptogen herb, its action is somewhat different from that of *Rodiola*. Modern chemical researches discovered it mainly contains saponin glycosides. Ever since the isolation and identification of a few ginsenosides such as Rb1 from *Gynostemma* in the 70s of the last century by Japanese researchers, the clinical applications of *Gynostemma*, in particular, its total saponin glycosides attracted increasing attention. Pharmacological experiments in animals showed a number of activities of *Gynostemma* extracts. *Gynostemma* effectively enhanced immune functions including specific and non-specific immunity. It was capable of helping maintain the stability of circulation system and thus protecting cardiovascular and blood system. And most noticeably, it had significant sedative, hypnotic and analgesic actions. Its ability in improving sleep will greatly help relieve insomnia and recover energy and is especially useful for the elderly. Because it is a natural product, long term administration will not cause drug dependence as seen in the use of hypnotics of single chemical entities. In addition it showed certain actions in anti-ageing.

*Lycium* has been used traditionally as an anti-ageing tonic, which is believed to be invigorating and able to delay ageing process. Pharmacological studies showed its strong action in strengthening and adjusting immunity and as a result it has been used as an adjuvant therapy for cancer. It also showed anti-oxidant activity by effectively scavenging free radicals, lipoperoxides, which are produced in large amount in the state of fatigue. This might be the mechanism of its anti-ageing action.

The combination of *Rhodiola, Gynostemma* and *Lycium* will have complementary advantages and synergistic effects to maximize the action comprehensively relieving the symptoms of fatigue as described below.

1) The "systematic correction" action of *Rhodiola* will help restore the normal functions of CNS, reduce such symptoms of fatigue as "slow response, poor judgment and depression", and improve the adaptive ability in unfavorable environment.
2) The sedative and hypnotic actions of *Gynostemma* will help improve sleep quality and this allows for a two-way approach, meaning "drug and self-recovery acting in parallel", to relieve fatigue more effectively.
3) With the combined actions of the 3 ingredients, i.e. the strengthening and regulating immune system, protecting cardiovascular system and clearing the toxic elements produced duo to fatigue, it becomes possible to get rid of all the fatigue symptoms.
4) It is worth noticing that the high dose of the composition of the present invention in animal experiment raised the accounts of blood red cells, platelet and hemoglobin responsible for carrying oxygen in blood. Those positive changes indicated that the normal dose of the said composition of the present invention might enhance the function of blood system and oxygen carrying capacity, resulting in relieving fatigue and restoring energy more effectively.

With the above mentioned benefits, the use of the said combination will allow for the reduction of the amount of individual herbs, minimizing the possible risk of side effects caused by long term administration of the single herb. And the net effect would be increased efficacy and safety. Besides, the reduced dose regime will make it more convenient for patients to take.

In another embodiment, the rational for the combination use of the 3 is further supported by the properties and functions of the individual herbs described in Chinese Materia Medca. *Rhodiola* was described as "qi-tonifying, blood-moving and circulation-promoting", *Gynostemma* "anti-inflammatory and detoxing" while *Lycium* can "strengthen kidney and liver, replenish vital essence to improve eyesight".

In another embodiment, the said composition may comprise plant raw material and/or mixture of plant extracts prepared by extracting each plant raw material separately and/or mixed plant extracts prepared by extracting mixed plant raw materials.

In another embodiment, in order to achieve better anti-fatigue effect, the said composition comprises 20-80% plant material from the genus *Rhodiola;* 10-60% *Gynostemma;* 10-60% *Lycium,* calculated on the basis of the dry weight of the raw materials and preferably, 30-50% from the genus *Rhodiola;* 20-40% *Gynostemma;* 20-40% *Lycium.*

According to plant taxonomy, plants from the same genus usually have similar chemical profiles even though they glow in different geographic areas. This feature allows for the use of different species from the same genus as the raw material for the same purpose. *Rhodiola* species in China are mainly distributed in the northeast, Gansu, Xinjiang, Sichuan, Tibet, Yunnan and Guizhou provinces. The species commonly used in medicine or health products include *Rhodiola sachalinensis* A. Bor., *R. rosea* L., *R. crenulata* (Hook. f. et Thoms.) H. Ohba, and *R. kirilowii* (Regel) Maxim.

In another embodiment, one or more of the afore said 4 species can be used for the manufacturing of the composition of the present invention, with *R. sachalinensis* as the preferred species.

In another embodiment the root and rhizome of *Rhodiola* plants are used as the raw material.

In another embodiment, the following species from the genus *Rhodiola* could also be used as alternatives to the above 4 species. In addition, there may be other *Rhodiola* species known to people in the art that can be used for the purpose of the present invention, which will still be within the scope of the present invention.

*R. alsia* (Frod.) S. H. Fu), *R. alterna* S. H. Fu, *R. angusta* Nakai, *R. aporontica* (Frod.) S. H. Fu, *R. atsaensis* (Frod.) H. Ohba, *R. atuntsuensis* (Praeg.) S. H. Fu, *R. brevipetiolata* (Frod.) S. H. Fu, *R. bupleuroides* (Wall. ex Hook. f. et Thoms.) S. H. Fu, *R. calliantha* (H. Ohba) H. Ohba, *R. chrysanthemifolia* (Levi.) S. H. Fu, *R. concinna* (Praeg.) S. H. Fu, *R. cretinii* (Hamet) H. Ohba, *R. dielsiana* (Limpr. f.) S. H. Fu, *R. discolor* (Franch.) S. H. Fu, *R. dumulosa* (Franch.) S. H. Fu, *R. eurycarpa* (Frod.) S. H. Fu, and *R. fastigiata* (Hook. f. et Thoms.) S. H. Fu Plants of the genus *Gynostemma* are widely distributed in China including all the provinces south of the Yangtze River, mostly cultivated. Among them the following 5 species contain higher content of saponin glycosides.

In another embodiment, one or more of the following 4 species can be used for the manufacturing of the composition of the present invention, with *G. pentaphyllum* being the preferred species.

*Gynostemma pentaphyllum* (Thunb.) Makino, *G. laxum* (Wall) Cogn., *G. pubescens* (Gagnep) C. Y. Wu, *G. gunagxiense* X. X. Chen et D. H. Qin, *G. compressum* X. X. Chen et D. R. Lians.

In another embodiment, the rhizome or whole herb of one or more of the above species can be used as the raw material in the manufacturing of the composition of the present invention.

In another embodiment, the following species from the genus *Gynostemma* could also be used as alternatives to the above 5 species. In addition, there may be other *Gynostemma* species known to people in the art that can be used for the purpose of the present invention, which will still fall within the scope of the present invention.

*G. aggregatum* C. Y. Wu et S. K. Chen, *G. burmanicum* King ex Chakr., *G. burmanicum* King ex Chakr. var. *molle* C. Y. Wu ex C. Y. Wu et S. K. Chen, *G. cardiospermum* Cogn. ex Oliv., *G. laxiforum* C. Y. Wu et S. K. Chen, *G. longioes* C. Y. Wu ex C. Y. Wu et S. K. Chen, *G. microspermum* C. Y. Wu et S. K. Chen, *G. palidinerve* Z. Zhang, *G. pentagynum* Z. P. Wang, *G. pentaphyllum* (Thunb.) Makino var. *dasycarpum* C. Y. Wu ex C. Y. Wu et S. K. Chen, *G. simplicifolium* Bl., *G. yixingense* (Z. P. Wang et Q. Z. Xie) C. Y. Wu et S. K. Chen.

In another embodiment, the following 3 *Lycium* species are used in the composition of the present invention, i.e. *L.*

*chinense* Mill., *L. dasystemum* Pojark and *L. barbarum* L which is listed in the Chinese Pharmacopoeia and also the preferred species for the purpose of the present invention.

In another embodiment, the dried ripe fruit of one or more of the above species are used to manufacture the composition of the present invention.

In another embodiment, the following species from the genus *Lycium* could also be used as alternatives to the above 3 species. In addition, there may be other *Lycium* species known to people in the art that can be used for the purpose of the present invention, which will still fall within the scope of the present invention.

*L. barbarum* L var. *auranticarpum* K. F. Ching, *L. chinense* Mill. var. *potaninii* (Pojarkova) A. M. Lu, *L. cylindricum* Kuang & A. M. Lu, *L. ruthenicum* Murray, *L. truncatum* Y. C. Wang and *L. yunnanense* Kuang & A. M. Lu In another embodiment, in order to achieve better efficacy of the composition of the present invention, it is necessary to extract the plant raw material with appropriate methods. If the plant parts to be used are roots or rhizomes, as in the case of *Rhodiola* and *Gynostemma*, they should be pulverized before extraction.

In another embodiment, the preferred extraction solvents in the present invention are water, low molecule alcohols or the mixture of the two although other solvents can also be used to obtain the active constituents from the plant materials.

In another embodiment, the manufacturing process of the active composition of the present invention comprises the following steps to obtain the dried extract at yields of 5-50%: extraction, filtration, concentration of the filtrate, drying and pulverization of the dried extract.

In another embodiment, with the consideration of possible toxicity of the residual solvent and cost, the preferred low molecular alcohol is ethanol of pharmaceutical or food grade.

In another embodiment, the extraction methods could include reflexing such as Soxhlet extraction, immersing at room temperature, percolation, ultrasonic extraction and microwave extraction but the preferred methods are reflexing and immersing at room temperature. In another embodiment, in order to extract the active constituents exhaustively the process involves a reflexing time of 1-3 hours, preferably 1-2 hours, for 1-5 times, preferably 2-3 times.

In another embodiment, the quantity of the extraction solvent is 5-18 folds, preferably 7-12 folds, of the weight of the raw plant material. In another embodiment, low temperature condensation under vacuum for the liquid extract is preferred to minimize the possible decomposition of the active constituents.

In another embodiment, the drying methods include drying under vacuum, spray drying, lyophilization and any other appropriate drying methods.

In another embodiment, the present invention provides a manufacturing method to obtain the extracts with higher purity of the active constituents, which includes the following steps. Add the concentrated extract liquid of *Rhodiola* or *Gynostemma*, obtained from the above mentioned process to an appropriate quantity of ethanol and make the final ethanol content to 50-80%, preferably 70%, stir thoroughly, allow to stand for 10-30 hours, preferably 20 hours, filter, collect the filtrate and condense the filtrate under vacuum, dry the extract, pulverize the dried extract which contains the active constituents of higher purity. The drying methods include drying under vacuum, spray drying and any other appropriate drying methods.

In another embodiment, the present invention also provides a manufacturing method to obtain the extracts with even higher purity of the active constituents, which includes the following steps. Dissolve the concentrated extract liquid of *Rhodiola* or *Gynostemma*, obtained from the above mentioned process to an appropriate quantity of a solvent, carry out column chromatography. Elute the column with appropriate solvent starting with solvent of low eluting ability, followed by one or more eluting solvents and collected the eluent which was then condensed under vacuum. The resulted in solid was dried and pulverized to obtain the extracts with even higher purity of the active constituents.

In another embodiment, the said column is packed with macroporous resin including but not limited to D-101, AB-8 and XDA-1, or polyamides, silica gel or any other substances which can be used for chemical separation.

In another embodiment, both gradient and constant concentration elution methods can be used.

As far as other techniques of column chromatography are concerned, they should be well known by people in the art.

In another embodiment, the drying methods include drying under vacuum, spray drying, lyophilization and any other appropriate drying methods.

In another embodiment, based on the characteristics of the plant raw materials and the active constituents herein, there could be two approaches to obtain the active constituents from the plant material.

The processes of the first approach is called "mixed extraction" involving the following steps: the 3 plant material are pulverized and then mixed according to the said ratio; the mixture was subjected to extraction using the said method; after concentration and drying, the extract of the composition of the present invention is obtained.

In another embodiment, the present invention provides the preferred approach, i.e. the second approach called "separate extraction" involving the following steps: pulverize and extract the 3 plant raw materials separately, the 3 extractives are subjected to purification, condensation and drying, respectively, to obtain 3 single extracts, each containing its own unique active constituents. Based on the yields of the dry extract from each plant material and the plant raw material ratio of the composition, weigh appropriate quantities of each single extract, mix well to obtain the composition of the present invention.

In another embodiment, in the composition of the present invention, the active constituents of each component plant have different physical and chemical properties. In order to extract the active constituents more effectively and ensure the high physiological activity of the composition of the present invention, it is recommended that ethanol water solution containing different concentrations of ethanl be used as extraction solvents to extract each plant separately as described in the above mentioned preferred (second) approach to manufacture the composition of the present invention.

In another embodiment, with the above mentioned method to obtain the separate extracts of the 3 herbs, the said composition can be described as comprising the following 3 extracts:

a) *Rhodiola* extract
b) *Gynostemma* extract
c) *Lyceum* extract

In another embodiment, it is a common knowledge that the above said individual extract would have different physical and chemical characteristics. The present invention provides herein the essential descriptions and quality requirements for each extract.

a) *Rhodiola* extract: pink colored powder with an acerbic taste containing 0.5-3.0%, preferably 0.8%-2.0%, salidroside. Limit tests: water<5.0%; heavy metals<10 ppm; total viable count<1000 cfu/g; *E. coli* and *Salmonelia*: negative.
b) *Gynostemma* extract: yellowish green powder with a bitter taste containing 20-80%, preferably 20-40%, gypenosides, with Rb1 as the reference chemical; Limit tests: water<5.0%; heavy metals<10 ppm; total viable count<1000 cfu/g; *E. coli* and *Salmonelia*: negative.
c) *Lycium* extract: brown powder with sour taste containing 20-60%, preferably 30-40% *lycium* polysaccharides with glucose as the reference chemical; Limit tests: water<5.0%; heavy metals<10 ppm; total viable count<1000 cfu/g; *E. coli* and *Salmonelia*: negative.

In another embodiment, to achieve the best efficacy of the composition of the present invention when made into medicaments, the oral doses should be adjusted according to the content of the active constituents in the exctarts, age, sex and body weight of the users. As a general guide, the daily dose for adult is recommended as 100-800 mg, preferably 150-600 mg, calculated on the basis of the dry weight of the total extract.

In another embodiment, the composition of the present invention prepared as described above can be combined with any pharmaceutically acceptable carriers to be made into any dosage forms administrated by potential consumers through any route but the preferred administration route is oral.

In another embodiment, when oral dosage form is selected, the following conventional excipients can be added to the composition of the present invention, including but not limited to: a) disintegrating agents such as dry starch, sodium carboxylmethyl starch, low-substitution hydroxypropyl methyl cellulose, crosslinking PVP, etc; b) lubricating agents such as magnesium stearate, talcum powder, sodium benzoate, polyethylene glycol (peg) 4000, etc; c) binding agents such as sodium carboxymethyl cellulose, sugar, gelatin, etc. One or more methods in pharmaceutics science can be used to manufacture any conventional oral dosage forms including but not limited to tablets, capsules or oral liquids, etc.

In another embodiment, the composition of the present invention can be made into solid or liquid soft drinks by the addition of flavouring agent, colouring, and stabilizing agent, etc. The said soft drinks can be carbonated or non-carbonated for anti-fatigue. The selection, amount of the said excipients herein are known to people in the art or decision can be made through a few simple experiments.

In another embodiment, the application of the composition of the present invention also include using the said composition as one of the constituents in a medicinal preparation, which contains the active components of the present invention and other substances such as botanical extracts and/or chemicals, and the finished product thereof is a mixture of the active components of the present invention and other medicinal substances. For instance, the composition or the mixed extract of the present invention can be used together with one or more vitamins, amino acids, minerals or any other substances that have is health and nutritional value to form a new recipe, which can be made into any of the above mentioned forms for the finished products for the purpose of anti-fatigue.

In another embodiment, rats were fed with the composition of the present invention for 30 days at doses 120 and 240 folds higher than human clinical doses (See Experiment 1) and generated the following results.

a) The test material did not have any impact on the general condition, body weight, liver and kidney functions;
b) The blood glucose levels of the female rats in both high and low dose groups and that of the male rats in high dose group were significantly lower than that of rats in the relevant comparison groups, respectively.
c) The blood cell counts, platelet counts and hemoglobin contents of the female rats in the test groups were significantly higher than that of rats in relevant comparison groups (p<0.01), respectively.
d) Histopathological examinations found no obvious toxic tissue pathological changes.

In another embodiment, short-term chronic toxicity study found that the recommended clinical dose range of the composition of the present invention was extremely safe.

In another embodiment, Ames Test with the said composition showed no sign of mutagenesis.

In another embodiment, the above experimental results demonstrated that the composition of the present invention could be used safely for a long period of time using the dose at the higher end of the recommended dose range to help lower blood glucose, increase red cell, platelet and hemoglobin of blood. The potential effect of the composition of the present invention in improving oxygen supply could be envisaged and as such a better anti-fatigue efficacy anticipated.

In another embodiment, the ultimate confirmation of the efficacy and safety of a potential medicine always comes from well-designed clinical trials in human. The inventors of the present invention carried out a randomized, double blind, placebo controlled clinical trial in 120 fatigue sufferers (See Experiment 3). The following brief summary of the trial results demonstrated that the composition of the present invention was a safe and effective medicine for the treatment of fatigue.

The test medicine in the trial containing the said composition did not cause any abnormal physiological changes in the participants but significantly reduced such typical fatigue symptoms as carebaria and headache, celostomia, difficult thinking and weary of talking. The participants in the treatment group receiving the test medicine had their sleeping quality and energy level greatly improved, when compared with the results from the placebo group. None of the participants in the test group showed any side effects as a result of taking the test medicine.

In another embodiment, apart from the demand for anti-fatigue products by people who are generally regarded as "healthy", many sufferers of chronic diseases can also benefit from taking anti-fatigue products and these include people with depression, congestive heart failure, anemia, hypothyroidism, diabetes, etc. Because of the long term suffering from the above chronic illnesses, they often experience fatigue. Taking some anti-fatigue products in conjunction with their conventional therapy will help them replenish vitality, enhance disease-resistance ability, improve general health and quality of life. Some of them may worry about the effect of the health products on the blood biochemistry, e.g. the blood glucose level of diabetes sufferers, and the possible incompatibility of anti-fatigue products with their conventional treatments. Moreover, many health products have no data from animal tests or clinical study to support their safety and efficacy in human use. By contrast, the safe and effective use in human of the composition and the relevant products containing the composition of the present invention is well documented through animal and clinical studies as described above.

In conclusion, the composition of the present invention containing the active constituents of plant species from genera of *Rhodiola, Gynostemma* and *Lycium* has the clear advantages of demonstrated anti-fatigue efficacy and safety in human use, controlled quality, and convenience in administration, and thus is more than likely to be accepted by the general public and health professionals alike.

EXAMPLES

Figure 1:
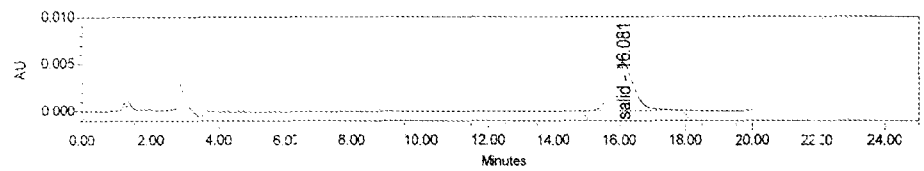
FIG. 1 HPLC results of Example 1.
Instruments: Waters HPLC instrument; Millennium 32 data process system; 600 pump; 2487 UV detector; PYE UNICAMPU 8800
UV/visible spectrophotometer.
Mobile phase: water-acetonitrile=95:5
Flow speed: 1 ml/min
Detection wavelength: 275 nm
Column: Sherisorb S100DS1, 250 mm×4.6 mm, 5 μm
Above: HPLC chromatogram of the standard reference chemical of salidroside
Lower: HPLC chromatogram of the sample in Example 1.
Figure 1:
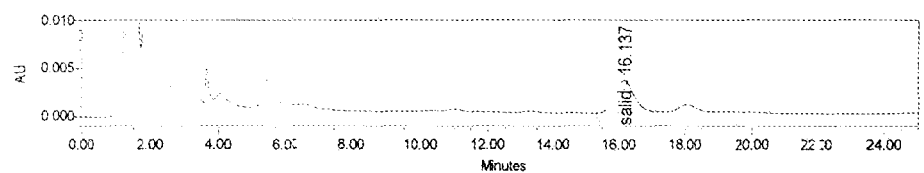
Figure 2:
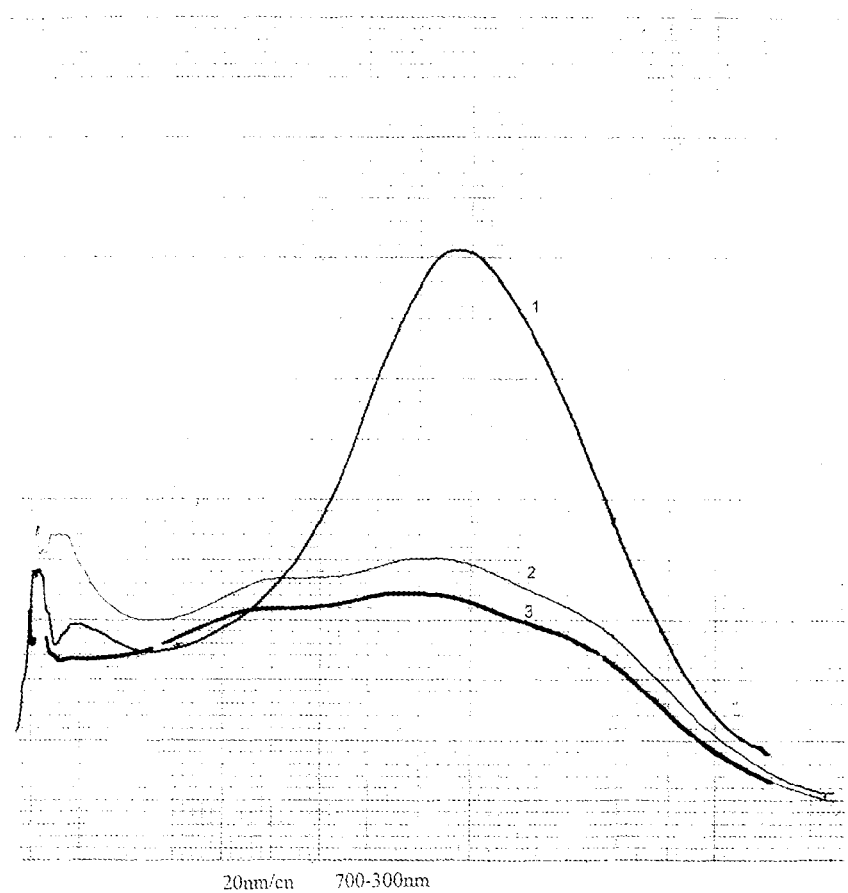
FIG. 2 UV absorption of the total gypenonsides from *G. pentaphyllum*
Instruments: PYE UNICAMPU 8800 UV/visible spectrophotometer
Reagents: Methanol, butanol, ammonia water, vanillin, glacial acetic acid and perchloric acid
Standard reference chemical: ginsenoside Rb1
Method: Accurately measure 100 μl methanol solution of the test sample into a 10 ml test tube with a plug, place it in a water bath to evaporate the solvent, immediately take it out of the water bath and to it add 0.2 ml, accurately measured, 5% vanillin solution in glacial acetic acid and 0.8 ml perchloric acid, shake well, place it in a 60° C. water bath for 15 minutes, cooling for 10 minutes under running water, add the 5 ml glacial acetic acid, shake well, measure at 300-700 nm wavelength.
In the Fig. Curve 1 represents the standard reference chemical; Curve 2 represents the total gypenosides sample from Experient 5; Curve 3 represents the total gypenosides sample from Experient 9; The resemblance of the absorptions of the 3 samples is indicative of their similarity.
Figure 3:
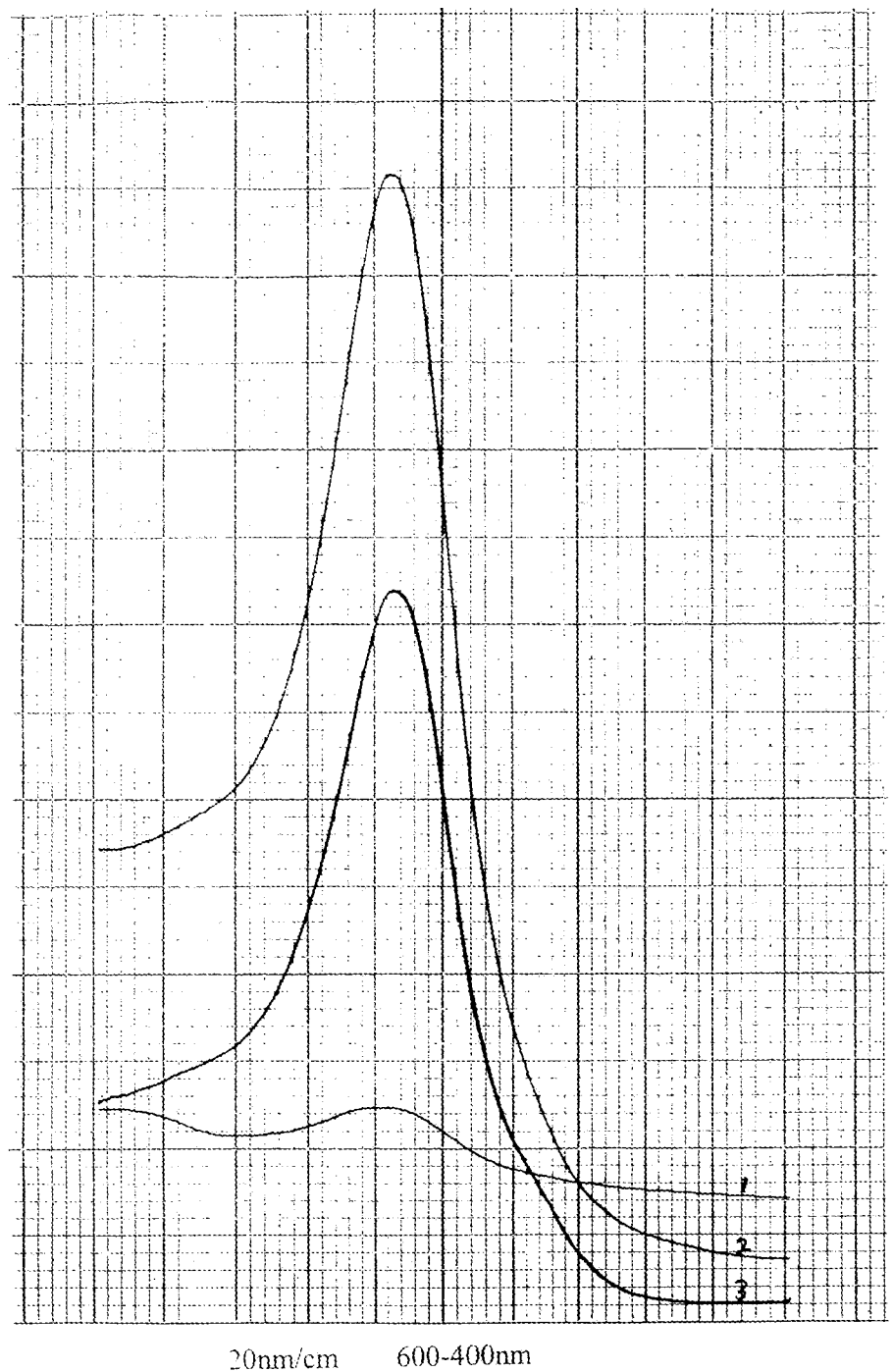
FIG. 3 UV absorption of the *Lycium* polysaccharides from Example 7
Instruments: PYE UNICAMPU 8800 UV/visible spectrophotometer
Reagents: sulfuric acid, water, phenol reagent
Standard reference chemical: glucose
Method: Measure accurately 1.0 ml water solution of the test sample into a 10 ml test tube with a plug, add water to 2.0 ml, add 1.0 ml phenol reagent, shake well, add 5.0 ml sulfuric acid, shake well and allow to stand for 5 min, heat it in a boiling water bath for 15 min, take it out and cool with cold water for 15 min. Measure at 400-600 nm wavelength.
In the Fig. Curve 1 represents the blank; Curve 2 represents the standard reference chemical; Curve 3 represents the test sample. The result indicated the presence of chemicals resemble to the reference standard chemical.

The following example are described herein only for the purpose of demonstrating the present invention but do not limit whatsoever the scope of the present invention.

Example 1

Pulverize 1000 kg raw material of *Rhodiola sachalinensis*, use a quantity of 50% ethanol, 4 folds of the raw material weight, to extract the pulverized material by reflexing for 4 times, extracting for 2 hours each time; Filter the combined extracted liquid and collect the filtrate, remove the solvent by condensation under vacuum; spray dry the condensed liquid to produce 325 kg *Rhodiola* extract containing 2.4% salidroside Example 2

Pulverize 1000 kg raw material of *Rhodiola rosea*, use a quantity of 70% ethanol, 4 folds of the raw material weight, to extract the pulverized material by reflexing for 4 times, extracting for 2 hours each time; Filter the combined extracted liquid and collect the filtrate, remove the solvent by condensation under vacuum; dry the condensed liquid under vacuum to produce 217 kg *Rhodiola* extract containing 0.8% salidroside.

Example 3

Dilute the condensed extract from Example 2 with an appropriate quantity of water; subject the resulting solution to D101 macroporous resin column chromatography; after the column being balanced with water, apply the solution through the column; elute with water and followed by 60% ethanol and collect the ethanol eluent; remove ethanol from the eluent; dry the condensed eluent under vacuum to obtain 65.2 kg dry extract containing 5.1% salidroside.

Example 4

Pulverize 100 kg the raw material of *Rhodiola crenulata*, mix it with 7 folds 70% ethanol and subject it to ultrasonic extraction for 40 min. at 40° C. and 40 KHz frequency; filter and collect the filtrate; add 5 folds 70% ethanol to the residue, ultrasonic extraction for 30 min., filter and combine the two filtrates; remove the solvent under vacuum and the resulting condensed liquid was spray dried to obtain 184 kg dry extract containing 3.0% salidroside.

Example 5

Pulverize 1000 kg raw material of *Gynostemma pentaphyllum*, use a quantity of 70% ethanol, 5 folds of the raw material weight, to extract the pulverized material by reflexing for 4 times, extracting for 2 hours each time; Filter the combined extracted liquid and collect the filtrate, remove the solvent by condensation under vacuum; dry the condensed liquid under vacuum to produce 188 kg *Gynostemma* extract containing 27.4% gypenosides.

Example 6

Dilute the condensed extract from Example 5 with an appropriate quantity of water; subject the resulting solution to AB-8 macroporous resin column chromatography; after the column being balanced with water, apply the solution through the column; elute with water and followed by 70% ethanol and collect the ethanol eluent; remove ethanol from the eluent; dry the condensed eluent under vacuum to obtain 65.2 kg dry extract containing 71.1% gypenosieds.

Example 7

Extract 1000 kg raw material of *Lycium barbarum* with 4 folds of water for 4 times, 1 hour each time; filter the extracted liquid and collect the filtrate which was condensed under vacuum to 0.5 g equivalent to the raw material per ml. Add the concentrated liquid to 5 folds of 95% ethanol while stirring, stir thoroughly and allow to stand for at least 12 hours; filter under vacuum; recover ethanol from the filtrate; wash the residue thoroughly with 95% ethanol; dry the residue under vacuum to obtain 160 kg *Lycium* extract containing 28.6% polysaccharides.

Example 8

Put the precipitate after "filter under vacuum" in Example 7 to 5 folds of water, stir to dissolve evenly, add slowly 0.2 mol/L cetyl trimethyl ammonium (CAT-OH) solution till pH 12, allow to stand overnight; separate the precipitate by centrifuging; add 35% acidic acid solution to the precipitate, stir to dissolve it thoroughly, filter and collect the filtrate; add to the filtrate 3 folds of 95% ethanol to precipitate, filter and collect the precipitate; wash it thoroughly with 95% ethanol and dry it under vacuum to produce 94 kg purified *Lycium* extract containing 54% polysaccharides.

Example 9

Mix well 1.40 kg *Rodiola* extract from Example 1, 0.55 kg *Gynostemma* extract from Example 5 and 0.45 kg *Lycium* extract from Example 7, fill the mixed extracts into size 2 capsules to produce 10000 filled capsules, each containing 240 mg extracts.

Example 10

Mix well 6.40 kg *Rodiola* extract from Example 3, 4.4 kg *Gynostemma* extract from Example 6 and 1.6 kg *Lycium* extract from Example 8, 1.7 kg microcrystalline cellulose, 0.45 kg crosslinking PVP, 0.55 kg CSM-Na, 0.05 kg magnesium stearate and 0.05 kg silica gel micro-powder, to produce 12000 tablets, with an average weight of 1.2 g of each tablet.

Example 11

Mix well 0.8 kg *Rodiola* extract from Example 4, 0.35 kg *Gynostemma* extract from Example 6 and 0.45 kg *Lycium* extract from Example 7, add appropriate amounts of white sugar, caramel colouring agent and essence; Dissolve the mixture in appropriate quantity of carbonated water; filter and sterilize the filtrate to obtain 3550 L carbonated drink to be filled into ring-pull cans of 355 ml capacity each.

Example 12

Mix well 2.78 kg *Rodiola* extract from Example 2, 1.80 kg *Gynostemma* extract from Example 5 and 1.60 kg *Lycium* extract from Example 7, add appropriate amount of sweetener, essence and soluble starch, granulate with ethanol, dry the granules and fill the granule into 10000 aluminum foil sachets; dissolve the content in water before drinking.

Example 13

Mix well 2.0 kg *Rodiola* extract from Example 2, 0.5 kg *Gynostemma* extract from Example 6 and 2.5 kg *Lycium* extract from Example 7, add appropriate amount of sweetener, essence, starch and lactose and make 10000 tablets.

Example 14

Mix well 4.1 kg *Rodiola* extract from Example 1, 0.5 kg *Gynostemma* extract from Example 5 and 0.5 kg *Lycium* extract from Example 8, add appropriate amount of sweetener, essence and soluble starch, granulate with ethanol, dry the granules and fill the granule into 10000 aluminum foil sachets; dissolve the content in water before drinking.

Example 15

Mix well 0.3 kg *Rodiola* extract from Example 1, 0.4 kg *Gynostemma* extract from Example 5 and 0.3 kg *Lycium* extract from Example 7, fill the mixed extracts into size 2 capsules to produce 3000 filled capsules.

Example 16

Mix well 0.8 kg *Rodiola* extract from Example 1, 0.1 kg *Gynostemma* extract from Example 5 and 0.1 kg *Lycium* extract from Example 7, fill the mixed extracts into size 2 capsules to produce 3000 filled capsules.

Example 17

Mix well 0.35 kg *Rodiola* extract from Example 1, 0.22 kg *Gynostemma* extract from Example 5 and 0.18 kg *Lycium* extract from Example 7, fill the mixed extracts into size 2 capsules to produce 2000 filled capsules.

Example 18

Mix well 0.60 kg *Rodiola* extract from Example 1, 0.13 kg *Gynostemma* extract from Example 5 and 0.13 kg *Lycium* extract from Example 7, fill the mixed extracts into size 2 capsules to produce 3000 filled capsules.

Example 19

Following the method in Example 1, obtain dry extract from 1000 kg *Rhodiola sachalinensis* raw material; following the method in Example 5, obtain dry extract from 3000 kg *Gynostemma pentaphyllum* raw material; and following the method in Example 7, obtain dry extract from 1000 kg *Lycium barbarum* raw material. Mix well the above 3 extracts, which was made into soft drinks based on the method in Example 11.

Example 20

Following the method in Example 1, obtain dry extract from 800 kg *Rhodiola sachalinensis* raw material; following the method in Example 5, obtain dry extract from 100 kg *Gynostemma pentaphyllum* raw material; and following the method in Example 7, obtain dry extract from 100 kg *Lycium barbarum* raw material. Mix well the above 3 extracts, which was granulated and packed based on the method in Example 14.

Example 21

Following the method in Example 1, obtain dry extract from 1500 kg *Rhodiola sachalinensis* raw material; following the method in Example 5, obtain dry extract from 2000 kg *Gynostemma pentaphyllum* raw material; and following the method in Example 7, obtain dry extract from 1500 kg *Lycium barbarum* raw material. Mix well the above 3 extract, which was made into tablets based on the method in Example 10.

Example 22

Following the method in Example 1, obtain dry extract from 500 kg *Rhodiola sachainensis* raw material; following the method in Example 5, obtain dry extract from 200 kg *Gynostemma pentaphyllum* raw material; and following the method in Example 7, obtain dry extract from 300 kg *Lycium barbarum* raw material. Mix well the above 3 extract, which was made into tablets based on the method in Example 10.

Example 23

Following the method in Example 1, obtain dry extract from 2000 kg *Rhodiola sachalinensis* raw material; following the method in Example 5, obtain dry extract from 2000 kg *Gynostemma pentaphyllum* raw material; and following the method in Example 7, obtain dry extract from 1000 kg *Lycium barbarum* raw material. Mix well the above 3 extracts, which was granulated and packed based on the method in Example 14.

Example 24

Following the method in Example 1, obtain dry extract from 1500 kg *Rhodiola sachainensis* raw material; following the method in Example 5, obtain dry extract from 1500 kg *Gynostemma pentaphyllum* raw material; and following the method in Example 7, obtain dry extract from 2000 kg *Lycium barbarum* raw material. Mix well the above 3 extracts, which was granulated and packed based on the method in Example 25-32

Using the same amount of raw materials, respectively, and following the same manufacturing method described in Example 9, the raw materials of different species in Examples 25-32 used to manufacture the extracts are listed in the table below, saving that any species from genera *Rhodiola*, *Gynostemma* and *Lycium* other than those listed below can be used in the same ways as described herein to manufacture corresponding extracts and relevant medicine, health products and food.

|  | *Rhodiola* raw material | *Gynostemma* raw material | *Lycium* raw material |
| --- | --- | --- | --- |
| Example 25 | *R. crenulata* | *G. laxum* | *L. dasystemum* |
| Example 26 | *R. kirilowii* | *G. laxum* | *L. dasystemum* |
| Example 27 | *R. sachalinensis* | *G. gunagxiense* | *L. dasystemum* |
| Example 28 | *R. rosea* | *G. gunagxiense* | *L. chinense* |
| Example 29 | *R. crenulata* | *G. compressum* | *L. barbarum* |
| Example 30 | *R. kirilowii* | *G. compressum* | *L. chinense* |
| Example 31 | *R. sachalinensis* | *G. pubescens* | *L. chinense* |
| Example 32 | *R. rosea* | *G. pubescens* | *L. barbarum* |

EXPERIMENTS

Experiment 1

Toxicity Test of the Composition of the Present Invention

1. Aim: Observe possible toxic effect in rats after 30 days continuous feeding with the composition of the present invention of different doses, if any, record the time of the onset, target organ and seriousness of the symptoms, to provide reference to determining the safe dose range for human use.
2. Animal: 66 Wistar rats, equal number in sex, body weight 150-170 g, provided by the Experimental Animal Centre of Chinese Academy of Medical Sciences. Quality Certificate No: MA01-3008.
3. Test sample: The mixed extract made Example 9, a deep brown powder with ethanol smell.
4. Method:
   4.1 Animal breeding: The rats were kept in the animal house of the institute, 5-6 each vinyon cage, temperature 20±2° C., RH 40-70%, natural light; granule rat feed provided by the Experimental Animal Centre of Chinese Academy of Medical Sciences; free feed and water intake; observe for one week before testing.
   4.2 Test sample preparation: Grind the sample to powder and add water to make suspension liquid of required concentration for adult rat enough for one day supply.
   4.3 Dose grouping and administration: Randomize rats into 3 groups of 22 with equal number in sex; rats in two test groups were given doses 5 g/kg and 10 g/kg, respectively, of the test sample and the third as comparison group; gavage administration once a day in the morning for 30 days.
   4.4 Outcome
      4.4.1 General: Observe every day rat behavior, feces and urine, toxic symptom, time of onset and lasting time; record the quantity of feed and water intake once a week; weigh each rat before testing and record the body weight once a week during the testing period and adjust the doses given accordingly.
      4.4.2 Blood routine examination: take blood from postocular is venous plexus at the end of the 30 day test period and measure RBC, WBC, Pit, Hb and leukocyte differential count. Instrument: SWELAB blood cell analyzer.
      4.4.3 Blood biochemistry: At the end of the test period, anesthetize rats with sodium pentobarbital; take blood from abdominal aorta and separate serum for blood biochemistry measurements, including AST, ALT, ALP, Cre, BUN, TP, ALB, Cho, T-Bill, Glu. The instrument used for the above measurements: Hitachi 7060 automatic biochemical analyzer; The test kids were provided by Beijing ZhongShen Hightech Ltd.
      4.4.4 System anatomy and histologic examination: After blood taking system anatomic examinations were carried out on the animals including: morphological changes, viscera index (weight of the organ/body weight×100%) obtained by isolating and weighing each organ, i.e. heart, liver, spleen, kidney, adrenal, brain, thymus, ovary, uterus, testicular, and prostate gland. Retain the appropriate tissues of the above organs and stomach, duodenum, jejunum, ileum, colon, lymph nodes, thyroid to be fixed in 10% formalin solution for histologic examination.
   4.5 Statistical methods: The data were analyzed using t-test and $X^2$-test.
5. Result and discussion:
   5.1 General and body weight changes: No abnormal behavior or activity of all the rats was observed with normal feces and urine during the test period. One rat was dead on day 6 from the 10 g/kg group; on day 15 one rat was dead from the 5 g/kg group. The autopsy found gastrointestinal bilge gas in both cases with no abnormality of heart, liver, spleen, lung, kidney and brain. The gastrointestinal bilge gas might be caused by the fermentation of the contents in the gut due to the long time gap between death of the rats (at night) and examination. Pathologic examination found obvious lung inflammation in the dead rat from 5 kg/kg group. The body weight increase at the end of week 3 of female rats and the end of week one of male rats in low dose group was found lower than that of rats in the comparison group (p<0.05). At the end of the test, the body weight increase was found the same across the 3 groups.

5.2 Impact on blood biochemistry (See Table 1): The blood glucose levels of the female rats in both high dose and low dose groups and of the male rats in high dose group were found to be significantly lower than that of rats in the comparison group, respectively (p<0.05, p<0.01); As for the liver function indicators, no significant difference in ALT and AST between the groups while the ALP of the female rats in both dose group was significantly higher than that of the rats in the comparison group (p<0.05). There was no significant change of BUN and Cre, indicators of kidney function. The Cho value of the female rats in the low dose group was significantly higher than that of the rats in comparison group (p<0.05).

7. Conclusion: The above results showed that the rats in both 5 g/kg and 10 g/kg groups did not suffer from obvious toxic reaction under the experiment condition. The lower dose of 5 g/kg used in the experiment is equivalent to 120 folds of a clinical dose 480 mg/day in human.

Experiment 2

Ames Test

1. Aim: Test the mutagenicity of the composition of the present invention by looking at its effect on the reverse mutation of histidine nutrition defected mouse *salmonella typhi*.
2. Test samples: The mixed extract made in Example 9, a deep brown powder with ethanol smell.
3. Bacteria strains: TA97, TA98, TA100*, TA102.
4. Method:
4.1 Medium preparation: pour the bottom layer of the medium containing 2% agar into a petri dish, cool and turn over, store in an incubator at 37° C. before use.

TABLE 1

Blood biochemistry changes after 30 days of feeding test

| | Doses (g/kg) | No. of rats | ALP (μ/L) | BUN (mmol/L) | Cre (μmol/L) | Glu (mg/dl) | Cho (mg/dl) |
|---|---|---|---|---|---|---|---|
| ♀ | 0 | 9 | 63.2 ± 22.3 | 6.2 ± 0.4 | 67.7 ± 12.0 | 133.1 ± 33.2 | 55.3 ± 10.7 |
| | 5 | 10 | 101.7 ± 27.7** | 5.4 ± 0.7** | 73.7 ± 6.4 | 105.4 ± 11.0* | 68.4 ± 8.1** |
| | 10 | 10 | 84.7 ± 18.9* | 5.8 ± 0.9 | 67.7 ± 4.4 | 94.8 ± 10.8** | 62.7 ± 8.2 |
| ♂ | 0 | 9 | 135.3 ± 35.1 | 5.8 ± 0.5 | 74.2 ± 10.0 | 127.2 ± 26.9 | 57.6 ± 8.5 |
| | 5 | 11 | 143.2 ± 17.0 | 6.1 ± 0.5 | 74.9 ± 5.9 | 113.6 ± 23.3 | 62.3 ± 10.5 |
| | 10 | 11 | 140.9 ± 23.5 | 5.3 ± 0.4* | 63.4 ± 4.0** | 95.2 ± 9.8** | 63.1 ± 5.5 |

*P < 0.05 against the comparison group,
**P < 0.01 against the comparison group 5.3 Blood routine examination (See Table 2): At the end of the test, the RBC, Pit and Hb of the female rats were significantly higher than that of the rats in the comparison group. There was an increasing tendency of those indicators in male rats in the test groups but with no statistic significance.

4.2 Bacteria incubation: Add 20 μl bacteria suspension to 5 ml nutrient broth, incubate at 37° C. with oscillation for 12 hours.
4.3 Dose grouping: Five doses were used, i.e. 5000 μg/dish, 2500 μg/dish, 1000 μg/dish, 100 μg/dish, 1 μg/dish, 3 dishes for each dose; one negative compari-

TABLE 2

Blood routine changes after 30 days of feeding test

| | Doses (g/kg) | No. of rats | RBC (×10$^{12}$/L) | WBC (×10$^9$/L) | HB (g/L) | Plt (×10$^9$/L) |
|---|---|---|---|---|---|---|
| ♀ | 0 | 11 | 5.17 ± 0.31 | 9.9 ± 1.6 | 117.1 ± 7.8 | 348.9 ± 141.5 |
| | 5 | 10 | 5.91 ± 0.38** | 9.1 ± 2.1 | 133.0 ± 8.1** | 524.2 ± 71.6** |
| | 10 | 10 | 6.11 ± 0.40** | 8.9 ± 3.2 | 135.2 ± 9.0** | 418.4 ± 46.5 |
| ♀ | 0 | 11 | 6.23 ± 0.53 | 9.9 ± 1.6 | 139.8 ± 11.8 | 371.9 ± 193.5 |
| | 5 | 11 | 6.65 ± 0.41 | 9.1 ± 2.1 | 145.5 ± 8.7 | 438.0 ± 105.5 |
| | 10 | 10 | 6.65 ± 0.55 | 8.9 ± 3.2 | 141.5 ± 9.1 | 429.7 ± 139.6 |

*P < 0.05 against the comparison group,
**P < 0.01 against the comparison group 6.4 Viscera indices and pathologic examinations: The kidney and adrenal indices of the rats in the high dose group were higher than that of rats in the comparison group. The viscera indices of the male rats in the low dose group were higher than that of rats in the comparison group. Pathologic examinations found no toxic pathological changes.

son group and one positive comparison group; use rat liver microsomal enzymes (S9) as in vitro activation system.
4.4 Plate application: Add 0.1 ml the incubated bacteria suspension and 0.1 ml test sample solution to the dish, shake in a 37° C. water bath for 20 min.; add the top potion of the medium, mix well. After solidification, turn over and incubate at 37° C. for 48 hours; count the reverse colony.

4.5 Criteria: The reverse colony count from the test sample is 2 times of that of the comparison group, and at the same time showing dose-dependent.

Conclusion: No mutation effect on all the 4 strains (See Table below)

rable body weight and age range; subjects in one group receiving the capsules containing the composition of the present invention while the other the capsules containing starch; Fatigue level was evaluated by the combination of FSC and physiological examinations. The study schedule is listed herein.

The effect of the composition of the present invention on the reverse mutation of histidine nutrition defected mouse *salmonella typhi.*

| | Bacteria strains | | | | | | | |
|---|---|---|---|---|---|---|---|---|
| | TA97 | | TA98 | | TA100 | | TA102 | |
| Group | −S9 | +S9 | −S9 | +S9 | −S9 | +S9 | −S9 | +S9 |
| C1 | 136.3 ± 5.1 | 186.7 ± 8.5 | 38.3 ± 3.2 | 44.7 ± 4.5 | 181.7 ± 5.7 | 194.7 ± 8.7 | 278 ± 10.4 | 287.3 ± 4.0 |
| C2 | 1703.0 ± 107.8 | 1397.0 ± 100.2 | 923.3 ± 59.4 | 793.3 ± 83.8 | 1317.0 ± 32.1 | 1625.0 ± 33.1 | 1337.7 ± 151.1 | 1306.7 ± 139.3 |
| 1 ug/dish | 126.7 ± 6.5 | 159.3 ± 6.8 | 38.0 ± 4.0 | 42.3 ± 6.0 | 178.0 ± 4.6 | 192.0 ± 12.1 | 281.0 ± 6.0 | 292.3 ± 7.0 |
| 100 ug/dish | 122.7 ± 6.7 | 147.0 ± 6.0 | 34.0 ± 3.6 | 42.0 ± 2.7 | 180.3 ± 12.9 | 186.3 ± 6.7 | 268.3 ± 11.0 | 283.0 ± 11.5 |
| 1000 ug/dish | 122.3 ± 9.5 | 128.0 ± 6.6 | 32.7 ± 4.0 | 37.7 ± 4.2 | 159.7 ± 9.0 | 169.0 ± 4.0 | 252.7 ± 8.6 | 262.0 ± 9.5 |
| 2500 ug/dish | 98.0 ± 11.5 | 109.3 ± 16.0 | 32.3 ± 4.6 | 39.3 ± 4.9 | 160.3 ± 4.7 | 171.7 ± 12.3 | 193.0 ± 5.6 | 200.3 ± 9.5 |
| 5000 ug/dish | 96.3 ± 5.0 | 109.7 ± 5.0 | 27.7 ± 5.5 | 32.0 ± 5.6 | 157.0 ± 12.7 | 161.7 ± 13.7 | 177.7 ± 16.6 | 183.0 ± 5.6 |

Notes:
C1 = negative comparison group;
C2 = positive comparison group
TA97 positive comparison: 2.0 μg/dish4-NQO(−S9), 10.0 μg/dish2-AF(+S9)
TA98 positive comparison: 20.0 μg/dish DMC(−S9), 20.0 μg/dish2, 7-2AF(+S9)
TA100 positive comparison: 2.0 μg/dish MMS(−S9), 10.0 μg/dish 2-AF(+S9)
TA102 positive comparison: 100.0 μg/dish paraplatin (±S9)

5. Conclusion: Ames test negative.

Experiment 3

Clinical Study

1. Aim: Study the clinical anti-fatigue efficacy and safety of the composition of the present invention.
2. Test samples: The capsules produced in Example 9 and placebo capsules containing starch.
3. Study institute: ShanXi medical University.
4. Subjects inclusion/exclusion criteria:
   a) Healthy volunteers with fatigue symptoms, aged between 50-60; Female subjects must be post-menopausal women;
   b) Have the informed consent form signed;
   c) Pass the Fatigue Symptom Check, FSC;
   d) Pass the routine checkup;
   e) Subject exclusion criteria: currently participating any clinical studies; serious illness sufferers; allergic to the test materials.
5. Dose and administration: each capsule contains either 0.24 g mixed extracts from Example 9 or starch, two capsules daily to be taken in the morning between 8:30 and 9:00.
6. Measurements:
   1) FSC questionnaire including 30 fatigue symptoms, which is regarded as one of the most comprehensive forms for measuring the subjective feeling of fatigue;
   2) Sleep quality questionnaire;
   3) Memory ability measurement;
   4) Physiological examinations.
7. Study design: randomize 120 qualified subjects into 2 groups, 30 male and 30 female each group with compa-

| | Day 1 | Day 11 | Day 21 |
|---|---|---|---|
| Health check | X | X | X |
| FSC Questionnaire | X | X | X |
| Sleep quality Questionnaire | X | X | X |
| Memory ability measurement | X | X | X |
| Checkup and blood routine | X | | X |
| Drug dispensing | X | | |
| Drug recovery | | | X |

8. Study result:
   1) Compared with the placebo group, some but not all of the fatigue symptoms of the subjects receiving the said composition were significantly reduced;
   2) Compared with the placebo group, the sleep quality of the subjects receiving the said composition were significantly improved including faster to fall asleep and reduced bedtime anxiety;
   3) Compared with the placebo group, there were no significant physiological changes observed before, during and after the study, which included the following examinations: body weight, blood pressure, heart rate, blood routine (Alt, Ast, Cre, Total protein, BUN, TC, TG, HDL-c, Blood glucose, RBC, Pit, and Hb) and blood adrenaline level.
   4) No any side effect found;
   5) FSC Questionnaire results which showed significant difference [above 80% confidence interval (c.i.)] between the groups and the efficacy of the test drug in "reducing feelings of fatigue" including:
      a) Carebaria (c.i. 96%)
      b) Tiredness (c.i. 88%)
      c) Weak legs (c.i. 98%)
      d) Wanting to be recumbent (c.i.87%)
      e) Feeling sleepy after meal (c.i.98%)
      f) Tired of talking (c.i.82%)
      g) Headache (c.i.96%)
      h) Stiff shoulders (c.i.80%)

6. The study results showed that the composition of the present invention significantly reduced fatigue symptoms and improved sleep quality without impact on the physiological indicators of the subjects. In addition, the products made from other Examples will also produce the results as described in experiments 1-3.

The invention claimed is:

1. A composition having anti-fatigue activity comprising plant extracts from the genera *Rhodiola, Gynostemma*, and *Lycium*, wherein the plant extracts are in the following concentrations based on dried weight:
    40-80% from the genus *Rhodiola*;
    10-50% from the genus *Gynostemma*;
    10-50% from the genus *Lycium*; and
    wherein the *Rhodiola* extract includes 0.5-3.0% salidroside, the *Gynostemma* extract includes 20-80% gypenosides, and the *Lycium* extract includes 20-60% *Lycium* polysaccharides.

2. The composition of claim 1, wherein the plant extracts comprise 40-50% from the genus *Rhodiola*, 20-40% from the genus *Gynostemma*, and 20-40% from the genus *Lycium*.

3. The composition of claim 1, wherein said *Rhodiola* comprise one or more of the species *Rhodiola sachalinensis* A. Bor., *R. rosea* L., and *R. crenulata* (Hook, f. et Thoms.) H. Ohba, *R. kinlowii* (Regel) Maxim; said *Gynostemma* comprise one or more of the species *Gynostemma pentaphyllum* (Thunb.), Makino, *G. laxum* (Wall) Cogn., *G. pubescens* (Gagnep) C. Y. Wu., *G. gunagxiense* X. X. Chen et D. H. Qin, and *G. compressum* X. X. Chen et D. R. Lians; and said *Lycium* comprise one or more of the species *Lycium barbarum* L., *L. chinense* Mill., and *L. dasysemum* Pojark.

4. The composition of claim 1, wherein said *Rhodiola* consist essentially of the species *Rhodiola sachalinensis*; said *Gynostemma* consist essentially of the species *Gynostemma pentaphyllum* (Thunb.), Makino; and said *Lycium* consist essentially of the species *Lycium barbarum* L.

5. The composition of claim 1, wherein said *Rhodiola* extract comprises 0.8-2.0% salidroside; said *Gynostemma* extract comprises 20-40% gypenosides; and said *Lycium* extract comprises 30-40% *Lycium* polysaccharides.

6. An anti-fatigue health product comprising an effective amount of the composition according to claim 1 and one or more excipients, wherein the health product is selected from the group consisting of a tablet, a capsule, an oral liquid, a food, and a drink.

7. A method of manufacturing the composition of claim 1, comprising the steps of:
    a) pulverization plant material from each of *Rhodiola, Gynostemma*, and *Lycium* plants;
    b) extracting the pulverized plant material with an extraction solvent;
    c) condensing the extracted liquid;
    d) drying of the condensed liquid to obtain a dried preparation; and
    e) mixing the dried preparation to obtain said composition.

8. The method of claim 7, wherein the extraction solvent comprises water, one or more low molecular-weight alcohols, or mixtures thereof.

9. The method of claim 8, wherein said extracting comprises reflexing for a period of 1-3 hours for 1-5 times, and wherein the quantity of the extraction solvent is 5-18 fold of the plant material.

* * * * *